US005430129A

United States Patent [19]

Campbell et al.

[11] Patent Number: 5,430,129

[45] Date of Patent: Jul. 4, 1995

[54] PURIFIED, NATIVE DYSTROPHIN

[75] Inventors: Kevin P. Campbell; Steven D. Kahl; James M. Ervasti, all of Iowa City, Iowa

[73] Assignee: University of Iowa Research Foundation, Iowa City, Iowa

[21] Appl. No.: 642,202

[22] Filed: Jan. 16, 1991

[51] Int. Cl.$^6$ .......................... C07K 3/20; C07K 3/22; C07K 3/10

[52] U.S. Cl. .................................... 530/395; 530/397; 530/413; 530/414; 530/416; 530/417

[58] Field of Search ............... 530/395, 397, 841, 413, 530/414, 416, 417

[56] References Cited

U.S. PATENT DOCUMENTS

| | | | |
|---|---|---|---|
| 4,912,202 | 3/1990 | Campbell et al. | 530/387 |
| 5,187,063 | 2/1993 | Campbell et al. | 435/7.21 |
| 5,239,060 | 8/1993 | Kunkel et al. | 530/350 |

OTHER PUBLICATIONS

Korsgren et al., Jour. of Biol. Chem., vol. 261(12), pp. 5536–5543, 1986.
Koenig et al., Cell, 53: 219–228 (1988).
Hoffman et al., Cell, 51: 919–928 (1987).
Ervasti et al., Nature 345: 315–319 (1990).
Campbell et al., Nature 338: 259–262 (1989).
Ervasti et al., J. Biol. Chem., 266: 9161–9165 (1991).
Ohlendieck, K. et al., J. Cell Biol. vol. 112, No. 1, Jan. 1991, pp. 135–148.
Campbell et al., Nature vol. 338, 1989, pp. 259–262.

*Primary Examiner*—David A Redding
*Assistant Examiner*—C. Sayala
*Attorney, Agent, or Firm*—Kevin M. Farrell

[57] ABSTRACT

The invention pertains to pure, native dystrophin of mammalian skeletal muscle and a method of purifying dystrophin from mammalian skeletal muscle. The invention further pertains to a method of diagnosing muscular dystrophy by detecting the loss or abnormal structure of pure, native dystrophin from mammalian skeletal muscle. The detection of a loss of dystrophin or an abnormal structure of dystrophin is indicative of muscular dystrophy.

6 Claims, 7 Drawing Sheets

Purification of Dystrophin

Solubilize Skeletal Muscle Membranes

↓ *1 % Digitonin*
*0.5 M NaCl*
*0.5 M Sucrose*
*Protease Inhibitors* sWGA Agarose

↓ *Elute column with 300 mM NAG*

DEAE Cellulose

↓ *Elute with increasing [NaCl]*

Alkaline Treatment

↓ *1 h, pH 11*

5 % - 20 % Sucrose Gradient

↓ *3 h at 200,000 x g*

WGA Sepharose 6MB

↓ *3 x 0.5 ml, O/N*

WGA Void
(Pure Dystrophin)

pH 7.4

224 —
109 —
72 —
46 —
29 —

1 2 3 4 5 6 7 8 9 10 11 12 13 14

Fraction pH 11

224 —
109 —
72 —
46 —
29 —

1 2 3 4 5 6 7 8 9 10 11 12 13 14

Fraction

CB

224 —
109 —
72 —
46 —
29 —

11 12 13 14 15 16 17 18 19 20
Fraction

WGA

224 —
109 —
72 —
46 —
29 —

11 12 13 14 15 16 17 18 19 20
Fraction

PURIFIED, NATIVE DYSTROPHIN

BACKGROUND OF THE INVENTION

Muscular dystrophy refers to a group of genetically determined myopathies characterized by progressive atrophy or degeneration of increasing numbers of individual muscle cells. The structural changes observed histologically are essentially the same in the various types of muscular dystrophies. This may, perhaps, suggest a common etiology. However, the distribution of the affected muscles is quite distinctive. This, along with the mode of inheritance, forms the basis of the classification of these diseases. The muscular dystrophies are traditionally subdivided by the patterns of initial muscle involvement, which in turn correlates fairly well with the type of genetic transmission. The three major forms of muscular dystrophy are as follows: 1) Duchennes Muscular Dystrophy which affects most skeletal muscle groups and is transmitted by an X-linked recessive gene; 2) Limb Girdle Muscular Dystrophy, affecting principally the pelvic and shoulder girdle muscles and is transmitted by an autosomal recessive gene; and 3) Facioscapulohumeral muscular dystrophy, involves the muscles of the face and shoulder girdle and is transmitted by an autosomal dominant gene.

Recently, the defective gene responsible for Duchenne muscular dystrophy (DMD) has been located on the X chromosome. The DMD gene encodes for a large molecular weight protein product called dystrophin. This protein is localized in the sacrolemmal membrane of normal skeletal muscle, but is absent from the skeletal muscle of people with DMD, as well as, dogs and mice with dystrophic muscle. A more benign form of this X-linked recessive disease is Becker's Muscular Dystrophy which is caused by an abnormal DMD gene which encodes an abnormal dystrophin protein. The exact function of dystrophin and the reasons why its absence or abnormal structure results in necrosis of dystrophic muscle fibers has not been determined. However, the amino acid sequence of dystrophin suggests that it is a membrane cytoskeletal protein.

The present technology for initial detection and diagnosis of Duchenne or Becker's Muscular Dystrophy relies on the use of an immunological probe to identify the presence of dystrophin, the absence of dystrophin, or the abnormal molecular weight or content of dystrophin in human muscle biopsies. Immunological assays, however, are indirect and often plagued by non-specific binding and/or cross-reactivity of the immunological probes (antibodies) with other proteins. Both of these problems can lead to false positive determinations. Conversely, other factors can cause interference with the binding of immunological probes with their target proteins (in this case, dystrophin). This type of problem can cause false negative determinations.

SUMMARY OF THE INVENTION

The invention pertains to pure dystrophin of mammalian skeletal muscle and a method of purifying said dystrophin. The invention further pertains to a method of diagnosing muscular dystrophy by detecting biochemically the loss or abnormal structure of purified dystrophin from mammalian skeletal muscle. The detection of a loss of dystrophin or an abnormal structure of dystrophin is indicative of muscular dystrophy.

In another embodiment, the invention provides a method for therapeutically treating a patient having a muscular dystrophic disease. This method comprises administering to the patient a therapeutically effective amount of purified, native dystrophin of skeletal muscle.

The present invention offers a novel and alternative means of diagnosing muscular dystrophy by allowing the direct detection of loss or abnormal structure of purified dystrophin. Current methods of detecting and measuring dystrophin include techniques which analyze dystrophin in a non-pure form while it is bound to other proteins and glycoproteins. These non-dystrophin compounds can interfere with indirect immunological methods of detection. The present invention overcomes these limitations and allows the direct analysis of pure, native dystrophin by biochemical and biophysical methods, as well as the immunological analysis of dystrophin without the interference of other bound proteins and glycoproteins. The availability of dystrophin in a pure, native form also provides better methods of prognosis and treatment for muscular dystrophy.

DETAILED DESCRIPTION

The techniques described herein are not limiting, but merely specific examples of techniques that can be employed in the purification and diagnostic methods of this invention.

Dystrophin is the large molecular weight protein product of the defective gene responsible for Duchenne muscular dystrophy. Native dystrophin exists as a component of a large oligomeric complex in the sarcolemmal membrane of normal skeletal muscle. Proteins and glycoproteins comprise the other components of this complex which is hereforewith referred to as the dystrophin-glycoprotein complex. Specifically, the other components comprise a 156 kDa glycoprotein, a 50 kDa glycoprotein, a 43 kDa glycoprotein, a 35 kDa glycoprotein and a triplet of proteins of 59 kDa molecular weight.

The present invention is based, in part, on the discovery of two techniques which greatly facilitate the purification of dystrophin from the dystrophin-glycoprotein complex of skeletal muscle membranes. First, it was discovered that succinylated wheat germ agglutinin (sWGA)-agarose substituted for WGA-sepharose resulted in dystrophin-glycoprotein complex preparations of the same purity and yield as previously known while obviating the need for an additional step involving sucrose gradient ultracentrifugation. Secondly, it was discovered that the purified dystrophin-glycoprotein complex is dissociated by alkaline treatment. Combining the novel 2-step purification of the dystrophin-glycoprotein complex using sWGA-agarose with alkaline dissociation of the complex resulted in purifying dystrophin to homogeneity. The term "pure, native dystrophin" refers herein to dystrophin that was purified by these methods from the dystrophin-glycoprotein complex as it exists naturally in mammalian skeletal muscle membranes. It is distinguished from DNA recombinant forms of dystrophin. This protocol required only commercially available materials and yielded protein in sufficient quantity to afford the necessary biochemical, functional and ultrastructural characterization of dystrophin.

Figure 1:
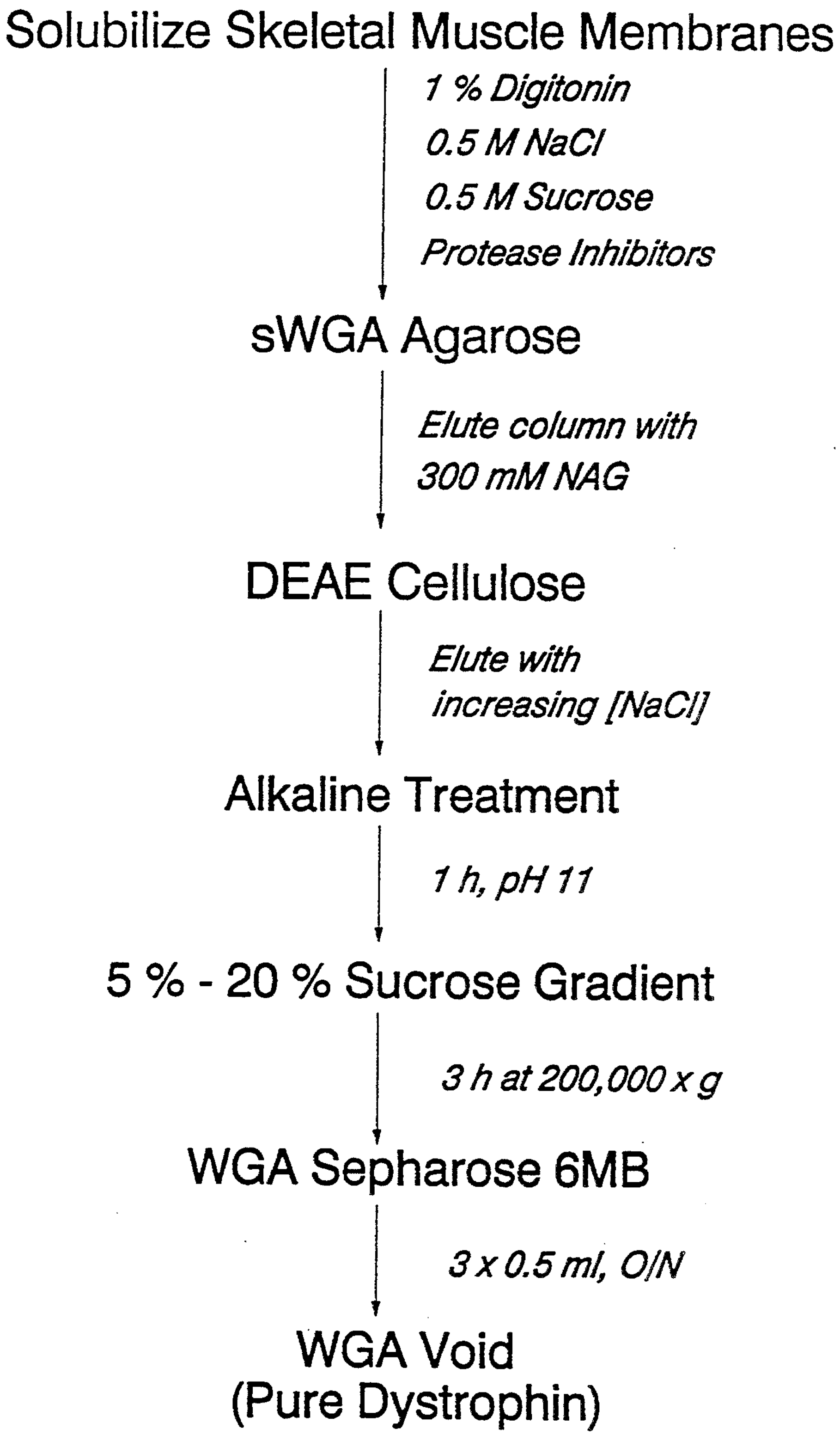
FIG. 1 is a flow diagram of the steps comprising the purification of hystrophin from mammalian skeletal muscle.

Dystrophin can be purified from the dystrophin-glycoprotein complex of detergent solubilized skeletal muscle membranes using lectin-affinity chromatography, ion exchange chromatography, alkaline treatment, and density gradient ultracentrifugation as illustrated in FIG. 1. Lectins are proteins or glycoproteins which specifically bind certain sugars or oligosaccharides. This property can be used to pick out certain glycoproteins from a complex mixture and is extremely useful as a general approach to the purification of membrane proteins, many of which are glycosylated. In the present invention, the linked components of the dystrophin-glycoprotein complex can be isolated as an intact complex with lectins that bind to the glycoprotein components of the complex. The lectins are typicaly coupled to a solid support such as a chromatographic gel (i.e., sepharose, agarose, etc.) and a complex mixture of solubilized membrane components is passed through a chromatography column containing the gel with bound lectin. The glycoproteins of membrane components bind to the lectin while the other components of the mixture pass through the column. Different lectins have different affinities for different glycoproteins.

It has been discovered that succinylated wheat germ agglutinin (sWGA) at physiological pH, does not bind N-acetylneuraminic acid, in contrast to WGA, which binds both N-acetylneuraminic acid and N-acetylglucosamine residues. Consequently, WGA binds the dystrophin-glycoprotein complex, as well as the skeletal muscle voltage-dependent sodium channel and the dihydropyridine receptor which are terminally sialated. On the other hand, succinylated WGA binds only the dystrophin-glycoprotein complex resulting in a greater degree of purity and obviating an additional step including sucrose gradient ultracentrifugation. Thus, sWGA can be used coupled to a chromatographic gel such as agarose (see Example I for greater detail) to isolate the dystrophin-glycoprotein complex in one simple step. Other lectin-chromatographic gels also can be used for purifying the dystrophin-glycoprotein complex, such as, Jacalin-agarose.

The dystrophin-glycoprotein complex can be further purified using ion exchange chromatography. If a protein has a net positive charge at pH 7, it will usually bind to a column of beads containing carboxylate groups, whereas a negatively charged protein will not. A positively charged protein bound to such a column can be eluted (released) by increasing the concentration of sodium chloride or another salt in the eluting buffer. Sodium ions compete with positively charged groups on the protein for binding to the column. Proteins that have a low density of net positive charge will tend to emerge first, followed by those having a higher charge density. Factors other than net charge, such as affinity for the supporting matrix, can also influence the behavior of proteins on ion-exchange columns. Negatively charged proteins can be separated by chromatography on positively charged columns such as diethyaminoethyl-cellulose (DEAE-cellulose) columns. Conversely, positively charged proteins can be separated on negatively charged columns such as carboxymethyl-cellulose columns. In the present invention, the negatively charged dystrophin-glycoprotein complex can be further purified using DEAE-cellulose and eluted with increasing sodium chloride.

The components of the purified dystrophin-glycoprotein complex can be dissociated and separated by alkaline treatment. The preferred embodiment of the present invention includes titration of the purified dystrophin-glycoprotein complex with one molar sodium hydroxide until the basicity of the sample reaches pH 11 and incubating the sample for one hour at 22° C. with mixing. Alternatively, the sample could be titrated with other basic substances at varying time periods and temperatures.

Dystrophin can be purified from the mixture of dystrophin-glycoprotein complex components by using density gradient ultracentrifugation. The sample following alkaline treatment is applied as a narrow band to the top of a solution in a centrifuge tube. To stabilize the sedimenting components of the sample against convection mixing, the solution beneath the band contains an increasing dense solution of an inert, highly soluble material such as sucrose (a density gradient). Under these conditions, the different fractions of the sample sediment at different rates forming distinct bands that can be individually collected. The rate at which each component sediments depends on its size and shape and is normally expressed as its sedimentation coefficient or S value.

Present day ultracentrifuges rotate at speeds up to about 80,000 rpms and produce forces up to about 500,000 x g. At these enormous forces, even relatively small macromolecules, such as small tRNA molecules and simple enzymes, separate from one another on the basis of their size. Using this technique, the size of alkaline treated dystrophin was estimated to be approximately 11 S by comparing its migration to that of known standards of varying size.

In order to completely purify dystrophin, the high $M_r$ glycoproteins which contaminated peak dystrophin-containing gradient fractions can be removed by WGA-sepharose adsorption using lectin-affinity chromatography as discussed earlier.

The average yield of pure dystrophin is 30 micrograms when 1.2–1.5 grams of skeletal muscle membranes are used as starting material. Based on previous estimates that dystrophin comprises up to only 0.002% of all muscle protein, this rapid method represents a 50,000-fold purification of dystrophin. One advantage of the present invention is that all of the chromatography matrixes used in this method are commercially available making the method accessible to all laboratories interested in studying the structure and function of dystrophin.

Following the alkaline treatment of the purified dystrophin-glycoprotein complex, an alternative form of affinity chromatography, known as immunoaffinity purification, can be used to isolate dystrophin. This technique utilizes the unique high specificity of antibodies both polyclonal and monoclonal. Antibodies are extremely valuable tools for rapid, selective purification of antigens. In principle, the antigen is coupled (immobilized) on a column support and this is used to selectively adsorb antigen from a mixture containing many other antigens. The antigens for which the antibody has no affinity can be washed away, and the purified antigen then eluted from its high affinity antibody with an elution buffer. In the present invention, antibodies directed to dystrophin can be used as the antibodies which are coupled to the column support and thus used for isolating dystrophin using immunoaffinity chromatography.

Monoclonal and polyclonal antibodies specific for pure, native dystrophin can be useful in the purification and diagnostic methods of this invention. Monoclonal antibodies useful in this invention can be obtained by well-known hybridoma methods. An animal is immunized with a preparation containing pure, native dystrophin. A fused cell hybrid is then formed between antibody-producing cells from the immunized animal and an immortalizing cell such as a myeloma.

In preferred embodiments, anti-dystrophin monoclonal antibodies of this invention are produced by murine hybridomas formed by fusion of: a) mouse myeloma or hybridoma which does not secrete antibody with b) murine spleen cells which secrete antibodies obtained from mice immunized against pure, native dystrophin.

Typically, the mice are immunized with a primary injection of pure, native dystrophin followed by a number of boosting injections of dystrophin. During or after the immunization procedure, sera of the mice may be screened to identify those mice in which a substantial immune response to dystrophin has been evoked. From selected mice, the spleen cells are obtained and fusions are performed. Suitable fusion techniques are the Sendai virus technique (Koehler, G., and Milstein, C., *Nature*, 256: 495 (1975)), or the polyethylene glycol method (Kennet, R. H., "Monoclonal Antibodies, Hybridomas—A new dimension in biological anaylsis," Eds. R. H. Kennet, T. J. McKern and K. B. Vectal, Plenum Press, N.Y. (1980)).

The hybridomas are then screened for production of anti-dystrophin antibodies. A suitable screening technique is a solid phase radioimmunoassay. A solid phase immunoadsorbant is prepared by coupling native, purified dystrophin to an insoluble matrix. The immunoadsorbant is brought into contact with culture supernatants of hybridomas. After a period of incubation, the solid phase is separated from the supernatants, then contacted with a labelled antibody against murine immunoglobulin. Label associated with the immunoadsorbant indicates the presence of hybridoma products reactive with native, purified dystrophin.

The monoclonal anti-dystrophin antibodies can be produced in large quantities by injection of anti-dystrophin antibody producing hybridoma cells into the peritoneal cavity of mice and, after an appropriate time, harvesting acites fluid from the mice which yield a high titer of homogeneous antibody. The monoclonal antibodies are isolated therefrom. Alternatively, the antibodies can be produced by culturing anti-dystrophin antibody producing cells in vitro and isolating secreted monoclonal anti-dystrophin antibodies from the cell culture medium directly.

Another method of forming antibody-producing cells is by viral or oncogenic transformation. For example, a B-lymphocyte which produced a dystrophin-specific antibody may be infected and transformed with a virus, such as the Epstein-Barr virus, to give an immortal antibody-producing cell. See Kozbon and Roder, *Immunology Today*, 4(3): 72–79 (1983). Alternatively, the B-lymphocyte may be transformed by a transforming gene or gene product.

Polyclonal antibodies can be prepared by immunizing an animal with a preparation of pure, native dystrophin. The animal is maintained under conditions whereby antibodies reactive with the native dystrophin are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g., IgG or IgM).

Anti-dystrophin antibodies also can be used in the development of immunoassays for the measurement of dystrophin. These assays can include radioimmunoassays, immunoradiometric assays, enzyme linked immunosorbent assays and others as described in Chard, T., An Introduction to Radioimmunoassay and Related Techniques, Elsevier Biomedical Press, Amsterdam, N.Y., Oxford (1986), hereby incorporated by reference and Voller, A., et al., The Enzyme Linked Immunosorbent Assay (ELISA): A guide with abstracts of microplate applications, Dynatech Laboratories, Alexandria, Va. (1979), hereby incorporated by reference. The measurement of pure, native dystrophin can occur following the alkaline treatment step for dissociating the components of the dystrophin-glycoprotein complex.

In the preferred embodiment of the diagnostic method of the invention, a muscle biopsy sample is treated in a procedure as described above for the purification of dystrophin. The amount of purified dystrophin is determined and expressed as a value relative to the amount of skeletal muscle starting material. The amount of dystrophin can be determined by assaying for protein content or by immunoassay. The levels of detection between normal samples and patient samples are compared. Levels of dystrophin lower than levels in normal skeletal muscle tissue are indicative of muscular dystrophy. An abnormal structure of pure, native dystrophin also is indicative of muscular dystrophy. Abnormal structure can be determined by various biochemical and biophysical methods, such as amino acid analysis, electron microscopy, x-ray crystallography, etc.

Muscle samples are obtained from patients by surgical biopsy. The site of biopsy could be any skeletal muscle suspected of being dystrophic. Muscle groups about the shoulder and pelvic girdles, however, are the most affected, and are likely to be the most common site of biopsy. The amount of muscle obtained should be enough to extract dystrophin from muscle membranes and detect its presence by the diagnostic methods described within this application. Alternative methods of extraction can be used.

Pure, native dystrophin can be used to treat patients having muscular dystrophies. Such treatments will involve the administration to the patient of a therapeutically effective amount of pure, native dystrophin. Administration of pure, native dystrophin can be by medically accepted techniques, including intravenous, enteral, etc., Appropriate amounts or dosages will vary from individual to individual and by the particular dystrophic disease. Appropriate dosages can be calculated in the art taking such factors into account.

The invention will now be illustrated by the following exemplifications.

EXAMPLE I PURIFICATION OF DYSTROPHIN-GLYCOPROTEIN COMPLEX

Heavy microsomes were prepared from rabbit skeletal muscle and washed twice with 0.6 M KCl in 50 mM Tris-HCl, pH 7.4, 0.165 M sucrose, 0.1 mM PMSF and 0.75 mM benzamidine to remove contractile proteins (Sharp, A. H., et al. *J. Biol. Chem.*, 262: 12309–12315 (1987), hereby incorporated by reference). 1.2–1.5 g of KCl-washed membranes were solubilized in 1.0% digitonin, 0.5 M NaCl, and protease inhibitors as previously described (Campbell, K. P. and Kahl, S. D., *Nature,* 338: 259–262 (1989), hereby incorporated by reference). The digitonin-solubilized membranes were circulated overnight on an 80 ml sWGA-agarose column (Vector Laboratories, Burlingame, Calif.), washed extensively with buffer A (0.1% digitonin, 50 mM Tris-HCl, pH 7.4, 0.75 mM benzamidine, 0.1 mM PMSF) containing 0.5 M NaCl (300 ml) followed by buffer A (300 ml), then eluted with 300 ml of 0.3 M N-acetylglucosamine in buffer A. Eluted fractions (4 ml each) containing dystrophin were applied to a 3 ml DEAE-cellulose column and sequentially eluted with the following NaCl concentrations in buffer A: 0 mM (40 ml), 25 mM (40 ml), 35 mM (40 ml), 50 mM (150 ml), 75 mM, (150 ml), 100 mM (200 ml), 110 mM (100 ml), 175 mM (40 ml) and 375 mM (40 ml). 4 ml fractions were collected from the 175 mM elution.

Lectins differ in sugar specificity. It was found that sWGA-agarose could be useful in the purification of dystrophin-glycoprotein complex. It is apparent from FIG. 1A that a high $M_r$ (400 kDa) protein was a major component of the proteins eluted from the sWGA-agarose with 0.3 M N-acetylglucosamine. The identification of this protein as dystrophin was confirmed on immunoblots with monoclonal and polyclonal anti-dystrophin antibodies. Densitometric analysis of the fractions shown in FIG. 1A indicated that dystrophin comprised 25% of the total protein compared to only 5% when WGA-sepharose was used. A small (approximately 10%) amount of dystrophin-glycoprotein complex was eluted from the sWGA-agarose column when washed with buffer A containing no NAGl. This material could be recovered after recirculation on a WGA-sepharose column. However, the majority of dystrophin was specifically eluted only when 0.3 M Noacetylglucosamine was included in the wash (FIG. 1A). The peak dystrophin-containing fractions eluted from the sWGA-agarose column (FIG. 1A were also enriched in proteins of 297 kDa, 109 kDa, 101 kDa, 88 kDa, a 59 kDa triplet, 50 kDa, a 43 kDa doublet, 35 kDa, 30 kDa and 25 kDa. The eluate from the sWGA-agarose column was devoid of sodium channel and dihydropyridine receptor which were major substituents of a similar elution profile from WGA-sepharose. The 109 kDa protein was identified as sarcoplasmic reticulum $Ca^{2+}$-ATPase using mAbs specific for this protein. However, neither the 109 kDa nor 101 kDa protein cosedimented with the dystrophin glycoprotein complex on sucrose gradients.

It was previously observed that ion exchange chromatography is useful in separating contaminants, particularly the sarcoplasmic reticulum $Ca^{2+}$-ATPase, from the dystrophin complex. When the dystrophin-enriched eluate from the sWGA-agarose column was applied to DEAE-cellulose and step-eluted with increasing NaGl concentrations, the 175 mM NaGl wash (FIG. 1B) was enriched in dystrophin and proteins of 88 kDa, a 59 kDa triplet, 50 kDa, a 43 kDa doublet, 35 kDa and 25 kDa, all previously detected in dystrophin-glycoprotein complex preparations. The 156 kDa dystrophin-associated glycoprotein is only faintly apparent as illustrated in FIG. 1B because it stains very poorly with Coomassie Blue, a phenomenon which has also been observed with the heavily glycosylated mucins and several erythrocyte membrane glycoproteins. The copurification of the 156 kDa glycoprotein with dystrophin was confirmed on immunoblots stained with mAb VIA$4_1$, which is specific for the 156 kDa glycoprotein. WGA-peroxidase stained nitrocellulose transfers of the DEAE-cellulose fractions eluting with 175 mM NaCl revealed the presence of several high $M_r$ glycoproteins ranging from 300 to 500 kDa which also contaminated dystrophin-glycoprotein complex prepared using WGA-sepharose. These high $M_r$ glycoproteins do not appear to be associated with dystrophin as they do not strictly cosediment with dystrophin on sucrose density gradients.

EXAMPLE II PURIFICATION OF DYSTROPHIN

Dystrophin-glycoprotein complex which eluted in the 175 mM NaGl wash (40 ml total volume) of Example I was concentrated to 0.6 ml in an Amicon stirred ultrafiltration cell (YM100 membrane, 25 psi), titrated to pH 11 with 1 M NaOH and incubated for 1 hr at 22° C. with mixing. 12.5 ml linear 5% to 20% (w/v) sucrose gradients containing 0.5 M NaGl in buffer A at the indicated pH were prepared using a BioComp Gradient Master density gradient former. The alkaline-treated dystrophin-glycoprotein complex was loaded onto a sucrose gradient containing 0.5 M NaGl in buffer A, pH 11 and overlayed with 0.1 ml of buffer A (pH 11) containing 0.5 M NAGl. Gradients were centrifuged at 4° C. in a Beckman VTI65.1 vertical rotor for the indicated time at 200,000 xg. Twenty 0.6 ml fractions were collected from the top of the gradients using an ISCO Model 640 density gradient fractionator. After centrifugation and fractionation, gradient fractions were titrated back to pH 7.4 with 1 M HCl. Sucrose gradient fractions 16–18 from a 3 h centrifugation of alkaline-treated dystrophin-glycoprotein complex were incubated for 2 h with 0.5 ml WGA-sepharose (Pharmacia LKB, Uppsala, Sweden) which had been pre-equilibrated in buffer A containing 0.5 M sucrose. The WGA-sepharose was pelleted and the supernatant (void) was incubated with three fresh 0.5 ml aliquots of WGA-sepharose over a period of 14 h. The resulting void, which contained pure dystrophin, was concentrated in a Centricon 100 and analyzed.

Polyclonal antisera against chemically synthesized peptides representing either the first 15 amino-terminal amino acids (MLWWEEVEDCYERED) or the last 10 carboxyl-terminal amino acids (PGKPMREDTM) of the predicted human skeletal muscle dystrophin sequence were raised in New Zealand white rabbits and affinity-purified against the immobilized synthetic peptides as described by Sharp and Campbell (Sharp, A. H. and Campbell, K. P., *J. Biol. Chem.*, 264: 2816–2825 (1989), hereby incorporated by reference). Neither of these affinity-purified antisera cross-reacts with a synthetic peptide representing the carboxyl-terminal 12 amino acids (CCPNVPSRPQAM) of the chromosome 6 dystrophin-related protein.

The dystrophin-glycoprotein complex isolated using WGA-sepharose as .the lectin matrices was shown to sediment as a large 18S complex on sucrose gradients. Likewise, the dystrophin-glycoprotein complex isolated using sWGA-agarose chromatography exhibited a sedimentation peak in fractions 10 and 11 of the 5%-20% sucrose gradient, a gradient profile identical to that observed for complex obtained via WGA-sepharose and run under identical conditions. Thus, it appears that the dystrophin-glycoprotein complex isolated using sWGA-agarose was of identical size, composition and purity as the preparation using WGA-sepharose without the need for a sucrose density gradient step.

Figure 2B:
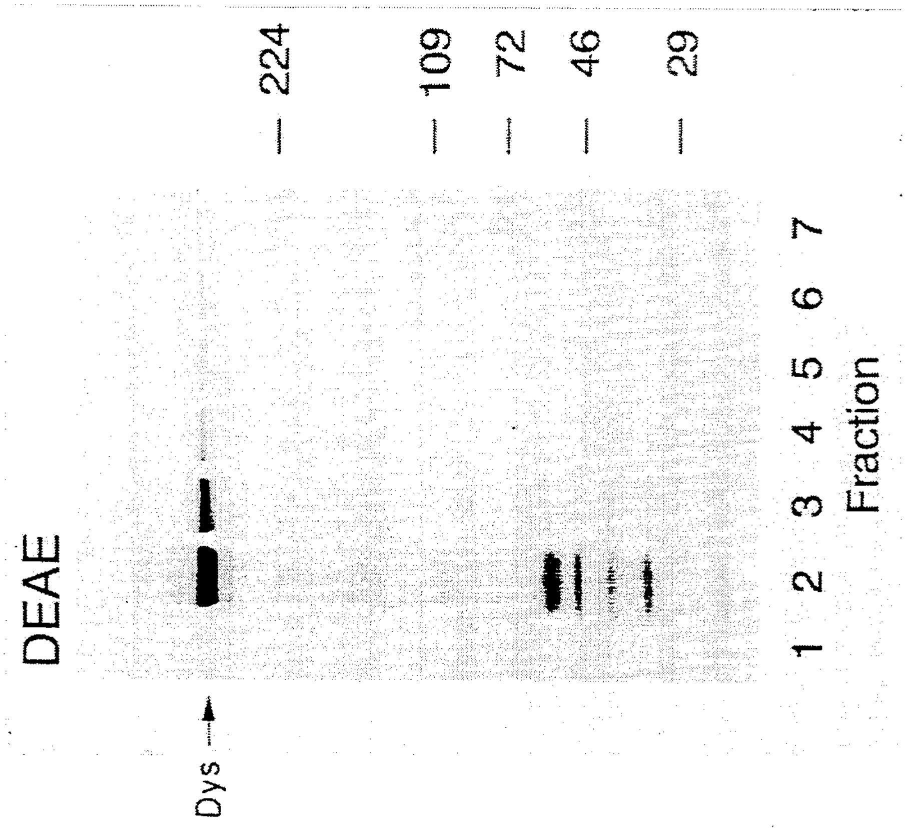
FIG. 2A and 2B depict the chromatographic purification of the dystrophin-glycoprotein complex by sWGA-agarose and DEAE-cellulose chromatography.
Figure 2A:
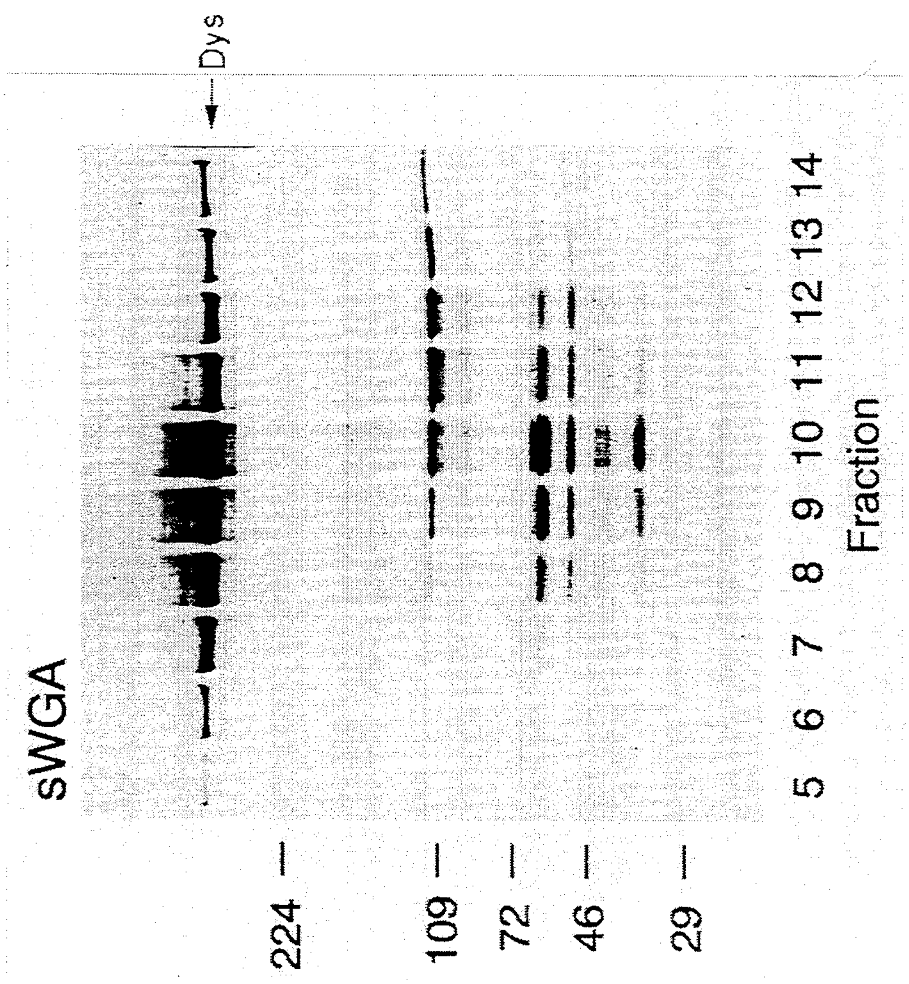

It was known that the dystrophin-glycoprotein complex could be disrupted by SDS or molar concentrations of K1 and recently, the purification of rabbit skeletal muscle dystrophin after SDS denaturation has been reported. However, SDS is essentially an irreversible denaturant and the removal of K1 requires prolonged dialysis. Therefore, the effectiveness of alkaline treatment in dissociating the dystrophin-glycoprotein complex was evaluated (FIG. 2). To test whether alkaline treatment could also dissociate the dystrophin-glycoprotein complex, purified dystrophin-glycoprotein complex (FIG. 1B) was concentrated, titrated to pH 11 with 1 M NaOH, and then centrifuged through a 5% to 20% linear sucrose gradient for 90 min. When the gradient profile of the alkaline-treated dystrophin-glycoprotein complex (FIG. 2B) is compared to the control gradient (FIG. 2A), it is apparent that the components of the alkaline-treated complex no longer cosediment and that all sediment as much smaller entities. These data indicate that the dystrophin-glycoprotein complex can be dissociated with alkaline treatment. In the absence of detergent, alkaline-treated dystrophin cosedimented with the 11S standard catalase on 15%-40% glycerol gradients which is in agreement with the sedimentation of tetrameric spectrin. This result indicates that alkaline-treated dystrophin sediments with a size consistent with a dystrophin dimer. This result also suggests that alkaline-treated dystrophin has not undergone extensive unfolding since it cosediments with spectrin, a protein with which it shares significant sequence and structural similarity. The 50 kDa dystrophin-associated protein sedimented near the top of the gradient and was completely separated from dystrophin (FIG. 2B). The sedimentation peak of the 156 kDa dystrophin-associated glycoprotein was found in fraction 5 as detected with mAb $VIA4_1$. However, the 50 kDa, 43 kDa, 35 kDa and 25 kDa dystrophin-associated proteins cosedimented possibly as a complex slightly smaller than dystrophin (FIG. 2B).

Figure 3A:
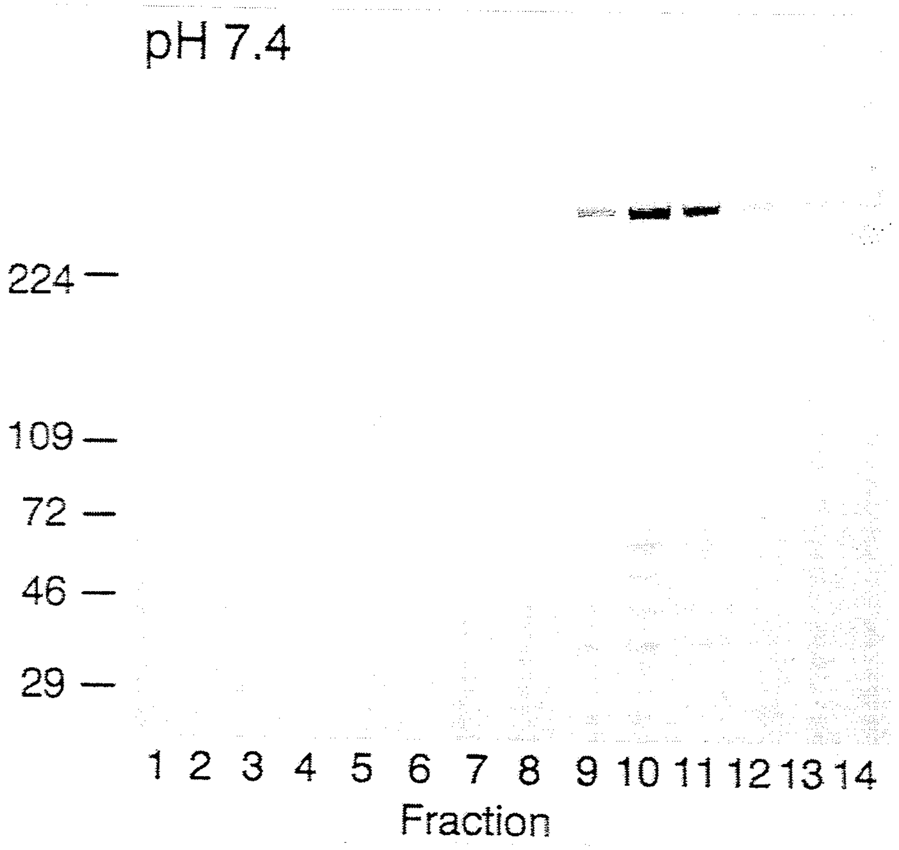
FIG. 3A and 3B represent polyacrylamide gels which depict the effect of alkaline treatment on sedimentation of the dystrophin-glycoprotein complex through 5% to 20% linear sucrose gradients.
Figure 3B:
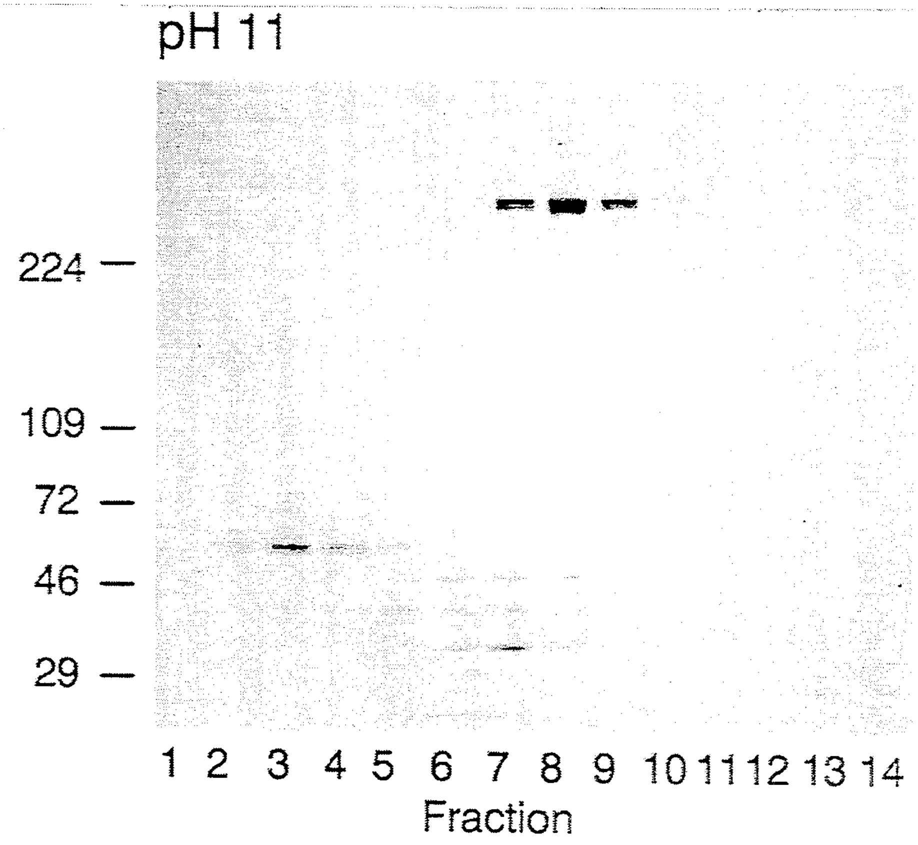
Figure 4A:
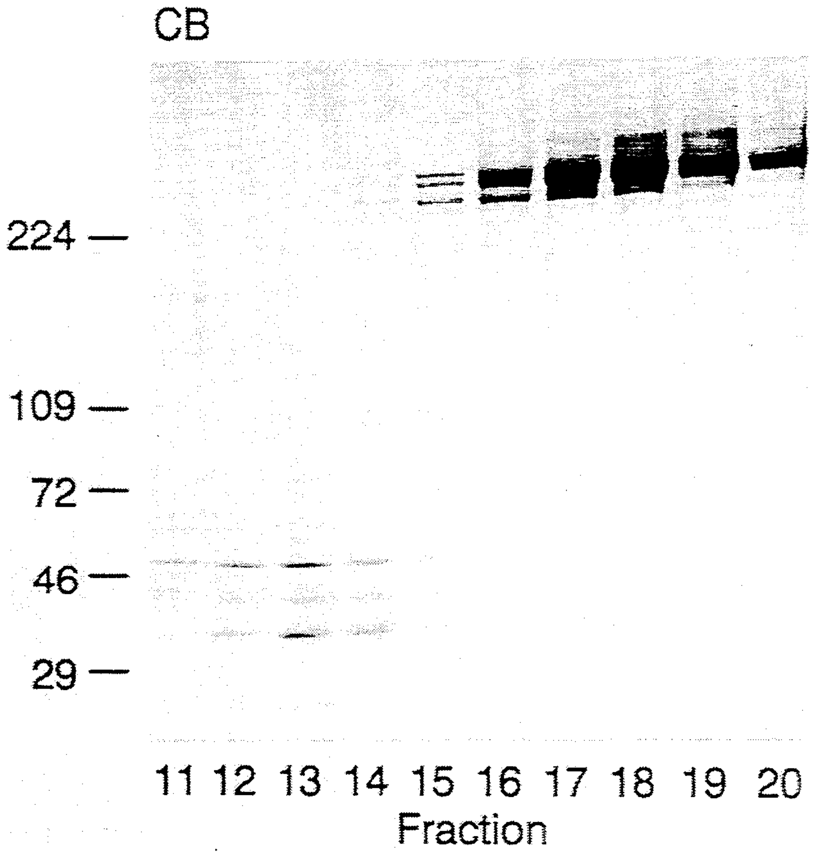
FIG. 4A and 4B represent polyacrylamide gels depicting the separation of dystrophin from dystrophin-associated proteins.
Figure 4B:
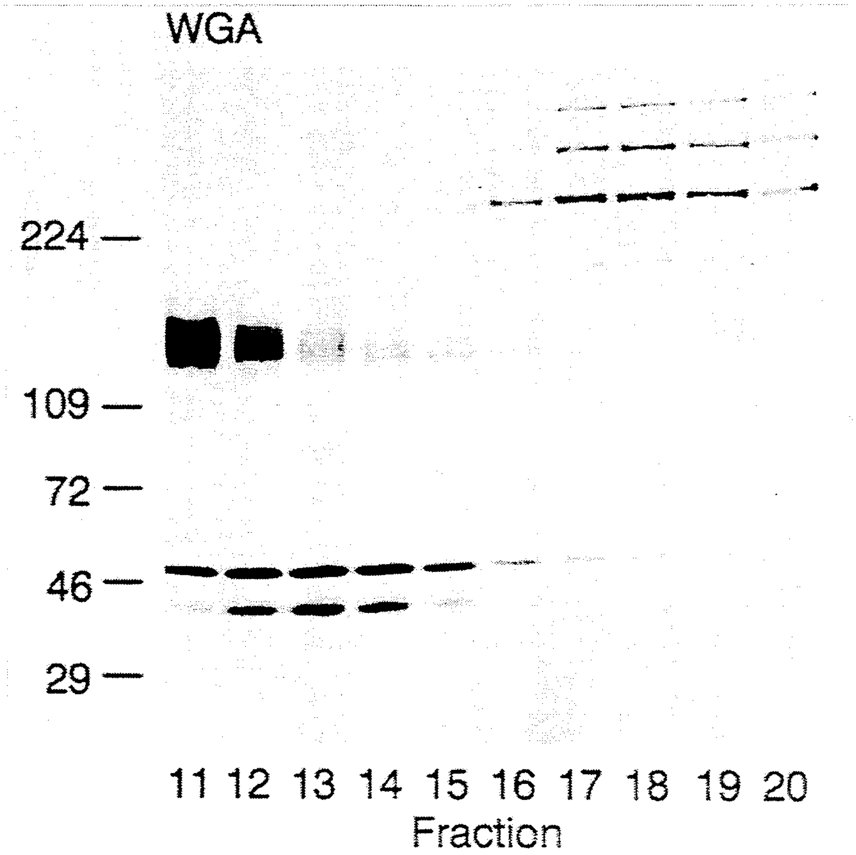
Figure 5A:
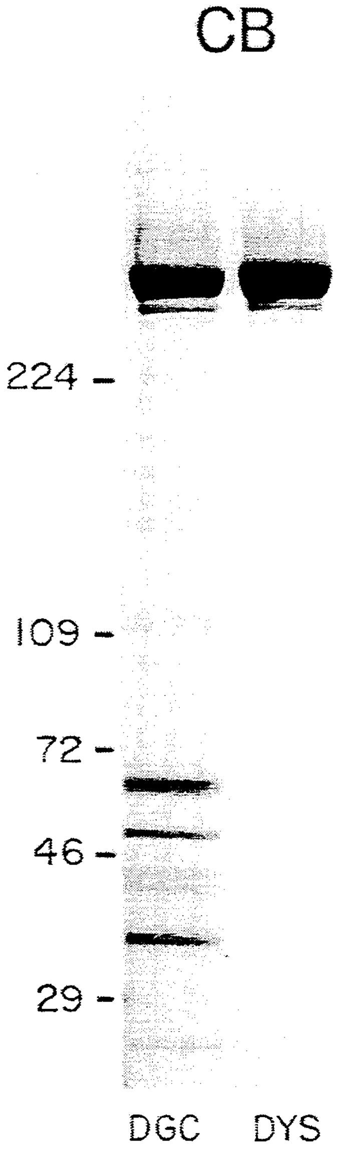
FIG. 5A and 5B represent, a polyacrylamide gel and FIGS. 5C and 5D a densitometric scan of said gel depicting the comparison of pure dystrophin to dystrophin-glycoprotein complex.
Figure 5B:
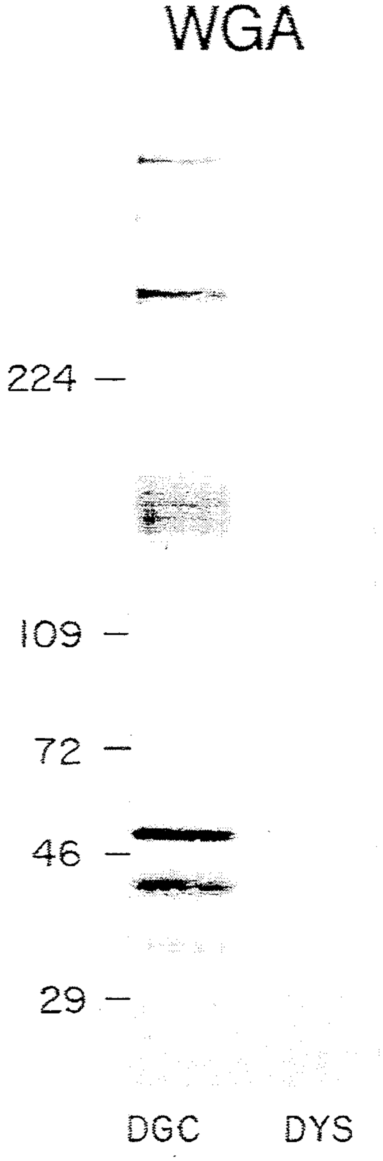
Figure 5C:
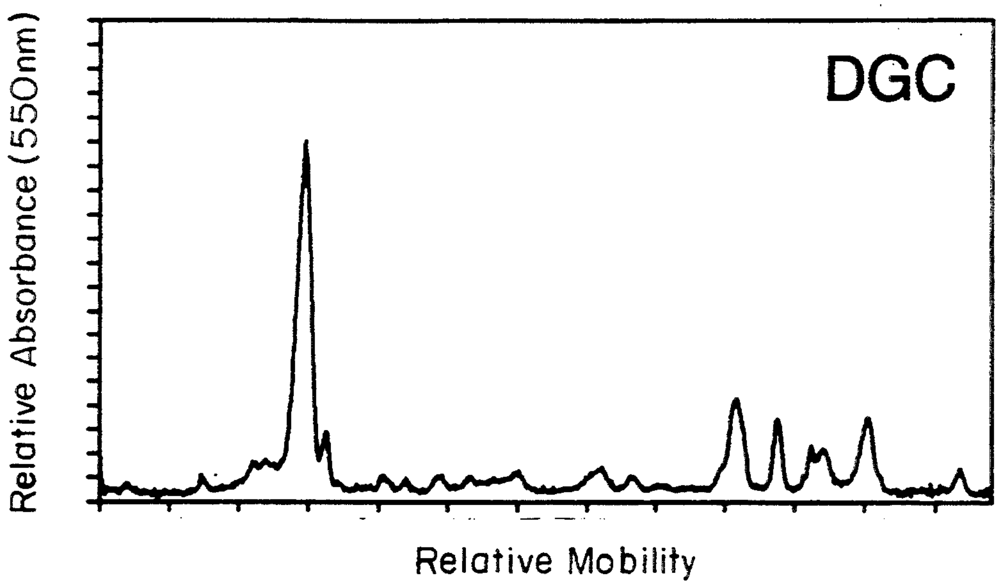
Figure 5D:
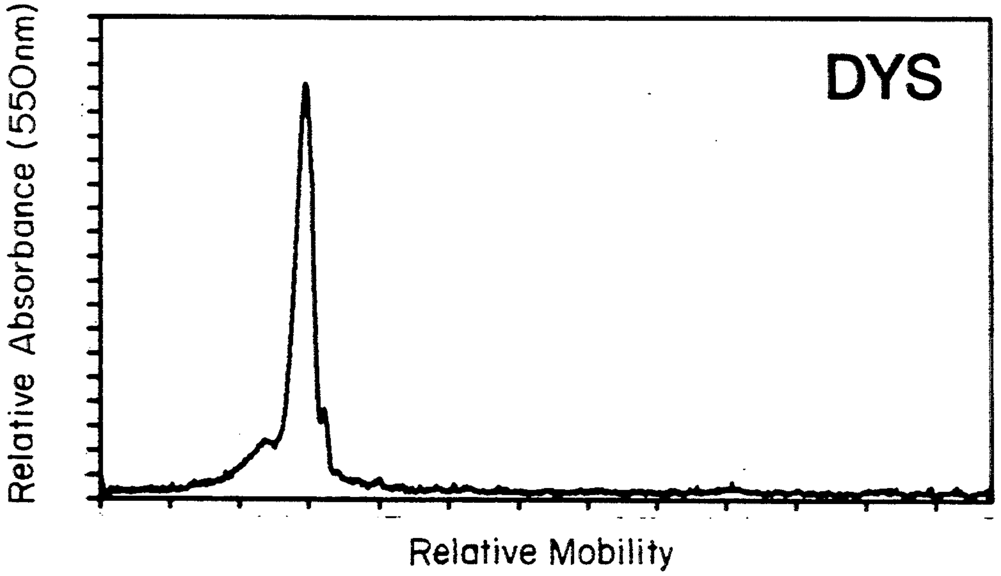
Figure 6A:
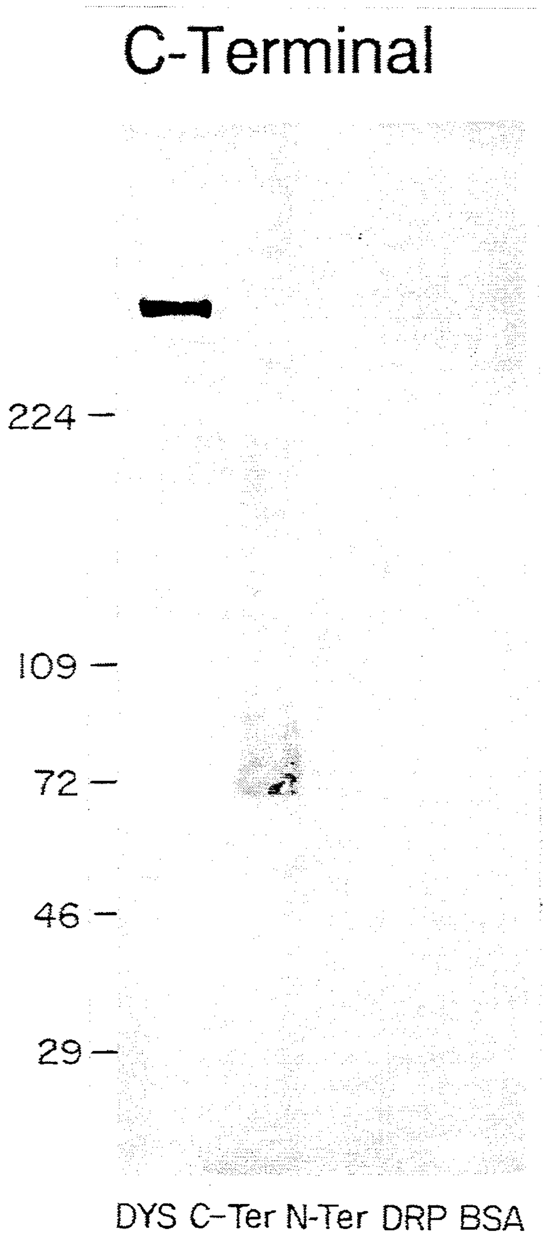
FIGS. 6A and 6B depict the immunoblot staining of pure dystrophin with human dystrophin sequence-specific, affinity purified polyclonal antisera.
Figure 6B:
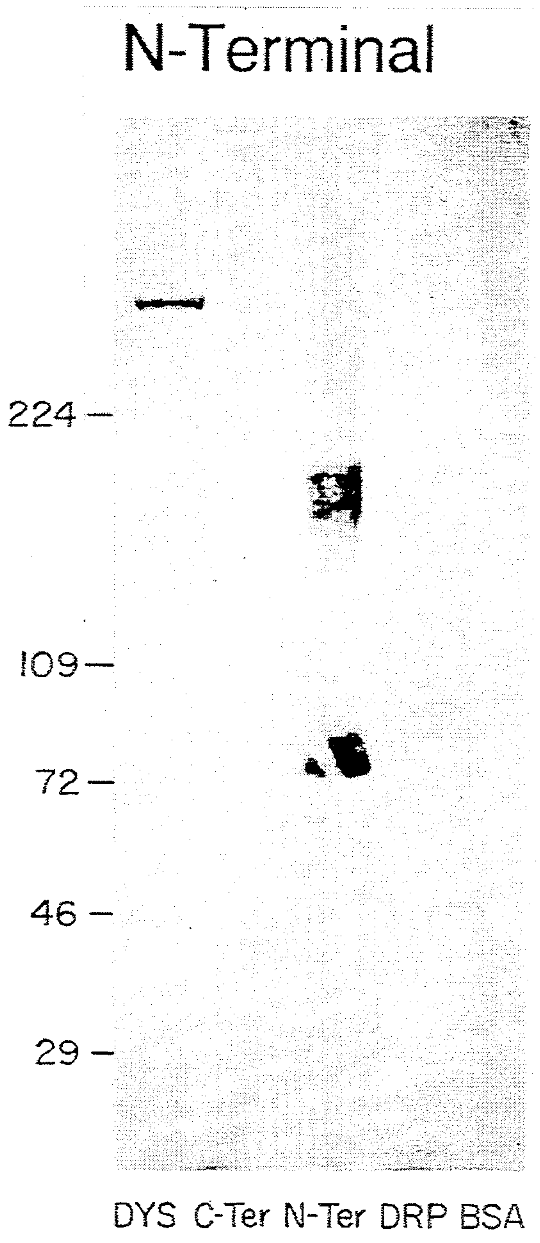

Alkaline treatment followed by a 3 h sucrose gradient centrifugation time (FIG. 3A) completely separated dystrophin from the 50 kDa, 43 kDa, 35 kDa and 25 kDa glycoprotein multiplet of the dystrophin-glycoprotein complex. However, this procedure was not sufficient to purify dystrophin from the high $M_r$ glycoproteins which contaminate dystrophin-glycoprotein complex preparations and cosediment with uncomplexed dystrophin (FIG. 3B). In order to completely purify dystrophin, the high $M_r$ glycoproteins which contaminated peak dystrophin-containing gradient fractions (FIG. 3B) were removed by WGA-sepharose adsorption (FIG. 4). Ninety-eight percent of the protein in the WGA void appeared as a single high $M_r$ band on overloaded Coomassie Blue-stained gels while the remaining 2% of protein composed a band of slightly lower $M_r$ (FIG. 4). Although it is difficult to accurately determine the $M_r$ of extremely large proteins by SDS-PAGE the predominant band in six consecutive preparations was calculated to have an average apparent $M_r$ of 400±6 kDa which is in close agreement with the predicted $M_r$. The predominant component appears to be intact dystrophin as it is recognized by antisera specific for either the amino-or carboxyl-terminals of human skeletal muscle dystrophin (FIG. 5). The minor, lower $M_r$ component in the dystrophin preparation was stained only by the carboxyl-terminal specific antisera (FIG. 5) indicating that it is most likely a proteolytic fragment. Also shown in FIG. 5, the affinity-purified carboxyl-terminal antisera does not recognize the synthetic peptide corresponding to the carboxyl-terminal of the chromosome 6 dystrophin-related protein. Nitrocellulose transfers stained with peroxidase-conjugated WGA revealed no contaminating glycoproteins in the pure dystrophin (FIG. 4). The average yield of pure dystrophin was 30 micrograms when 1.2-1.5 of rabbit skeletal muscle membranes was used as starting material.

Equivalents

Those skilled in the art will recognize, or be able to ascertain using no more than routine experimentation, many equivalents to the specific embodiment of the invention described specifically herein. Such equivalents are intended to be encompassed in the scope of the following claims.

We claim:

1. A method of purifying native, mammalian dystrophin, comprising the steps of:

a) obtaining a muscle sample;

b) isolating muscle membranes;

c) detergent-solubilizing the muscle membrane sample; and d) purifiying dystrophin from the sample by chromatography, alkaline treatment and sucrose density gradient centrifugation.

2. A method of purifying native, mammalian dystrophin, comprising the steps of:

a) obtaining a muscle sample;

b) isolating muscle membranes;

c) detergent-solubilizing the muscle membrane sample;

d) performing lectin-affinity chromatography and ion-exchange chromatography on the solubilized sample;

e) dissociating the components of the sample with alkaline treatment;

f) separating the components of the sample by sucrose gradient ultracentrifugation; and g) purifying dystrophin from the sample by lectin-affinity chromatography.

3. A method of purifying native, mammalian dystrophin, comprising the steps of:

a) obtaining a muscle sample;

b) isolating muscle membranes;

c) detergent-solubilizing the muscle membrane sample;

d) performing lectin-affinity chromatography and ion-exchange chromatography on the solubilized sample;

e) dissociating the components of the sample with alkaline treatment; and f) purifying dystrophin from the sample by immunoaffinity chromatography.

4. A method for purifying native, mammalian dystrophin, comprising the steps of:

a) providing purified dystrophin-glycoprotein complex;

b) disrupting the dystrophin-glycoprotein complex by contacting the dystrophin-glycoprotein complex with an alkaline solution;

c) separating the components of the disrupted dystrophin-glycoprotein complex; and d) recovering the purified native dystrophin component from the separated mixture of components.

5. A method of claim 4 wherein the alkaline solution has a pH of about 11.

6. A method of claim 4 wherein the components of the disrupted dystrophin-glycoprotein complex are separated by density gradient ultracentrifugation.

* * * * *